United States Patent
Guo et al.

(10) Patent No.: US 11,312,983 B2
(45) Date of Patent: Apr. 26, 2022

(54) GREEN PREPARATION METHODS OF RICE RESISTANT STARCH

(71) Applicant: Qilu University of Technology, Jinan (CN)

(72) Inventors: Li Guo, Jinan (CN); Hui Li, Jinan (CN); Bo Cui, Jinan (CN)

(73) Assignee: Qilu University of Technology, Ji'nan (CN)

( * ) Notice: Subject to any disclaimer, the term of this patent is extended or adjusted under 35 U.S.C. 154(b) by 104 days.

(21) Appl. No.: 16/850,580

(22) Filed: Apr. 16, 2020

(65) Prior Publication Data

US 2020/0332326 A1 Oct. 22, 2020

(30) Foreign Application Priority Data

Apr. 16, 2019 (CN) .......................... 201910303541.4

(51) Int. Cl.
  *C12P 19/04* (2006.01)
  *C12P 19/16* (2006.01)
  *C12P 19/18* (2006.01)
  *C12P 19/22* (2006.01)

(52) U.S. Cl.
  CPC .............. *C12P 19/04* (2013.01); *C12P 19/16* (2013.01); *C12P 19/18* (2013.01); *C12P 19/22* (2013.01)

(58) Field of Classification Search
  CPC   C12P 19/18; C12P 19/16; C12P 19/22; C12P 19/04
  See application file for complete search history.

(56) References Cited

U.S. PATENT DOCUMENTS

2021/0222218 A1* 7/2021 Guo ...................... A61K 9/2054

OTHER PUBLICATIONS

Ao et al., Starch with a Slow Digestion Property Produced by Altering Its Chain Length, Branch Density, and Crystalline Structure. J. Agric. Food. Chem., 2007, vol. 55: 4540-4547. (Year: 2007).*
Li et al., In vitro digestibility of rice starch granules modified by β-amylase, transglucosidase and pullulanase. Int. J. Biol. Macromol., 2019, vol. 136: 1228-1236. (Year: 2019).*
Miao et al., Dual-enzymatic modification of maize starch for increasing slow digestion property. Food Hydrocolloids, 2014, vol. 38: 180-185. (Year: 2014).*
Niu et al., Highly efficient enzymatic preparation of isomalto-oligosaccharides from starch using an enzyme cocktail. Electronic J. Biotechnol., 2017, vol. 26: 46-51. (Year: 2017).*
Perera et al., Resistant starch: A review of analytical protocols for determining resistant starch and of factors affecting the resistant starch content of foods. Food Res. Int., 2010, vol. 43: 1959-1974. (Year: 2010).*
Shi et al., Physicochemical properties, structure and in vitro digestion of resistant starch from waxy rice starch. Carbohydrate Polymers., 2011, vol. 84: 1151-1157. (Year: 2011).*

* cited by examiner

*Primary Examiner* — Ganapathirama Raghu

(57) ABSTRACT

Green preparation methods of rice resistant starch are disclosed. In some embodiments, a green preparation method of the rice resistant starch is characterized in that, at a temperature lower than the gelatinization temperature, the rice starch is sequentially modified by enzymes using β-amylase, glucosidase, and pullulanase to obtain the modified starch. In other embodiments, a green preparation method of the rice resistant starch is characterized by using: rice starch as a substrate; and in turn using: (a) β-amylase (BA, EC 3.2.1.2) from barley (*Hordeum vulgare*); (b) glucoside transferase (TG, EC 2.4.1.24) from *Aspergillus niger*; and (c) pullulanase (PUL, EC 3.2.1.41) from *Pullulanibacillus konaensis* below a gelatinization temperature to modify a chain structure of the rice starch, resulting in a number of short linear chains which are effectively arranged, aggregated, and recrystallized at 4° C. to form modified rice starch with high resistant starch content.

6 Claims, 3 Drawing Sheets

GREEN PREPARATION METHODS OF RICE RESISTANT STARCH

CROSS REFERENCE TO RELATED APPLICATIONS

This application claims priority to Chinese application number 20191030354-1.4 filed on Apr. 16, 2019, the disclosure of which is incorporated by reference herein in its entirety.

FIELD OF THE DISCLOSURE

The disclosure relates generally to production processes of resistant starch. More specifically, the disclosure relates to green preparation methods of rice resistant starch.

BACKGROUND

As a major source of human nutrition and energy, rice tends to cause hyperglycemic excursion because it is easily digested and absorbed. Therefore, how to lower postprandial blood glucose levels of the rice has been a hot spot of research on staple food and nutrition. According to the in vitro enzyme digestion rate of starch, the starch is divided into three primary parts: rapidly digestible starch (RDS), slowly digestible starch (SDS), and resistant starch (RS). RDS refers to the portion of starch rapidly digested within the first 20 min. SDS is the portion of starch digested between 20 and 120 min, which can be digested completely but slowly. RS refers to the portion of starch which is indigestible in the small intestine and is partially fermented into abundant short-chain fatty acids in the large intestine. The starch can control obesity and diabetes and reduce the risk for cardiovascular diseases.

Postprandial hyperglycemic levels of the rice are primarily due to the starch which accounts for approximately 90% of the dry weight of the rice. Modification of a molecular structure of the starch results in an increase in RS level and a decrease in glycemic index of a starch-based product. Generally, the RS level increases when the starch is treated with pullulanase. This is because pullulanase cleaves an α-(1→6)-glycosidic bond of the starch and transforms an external chain of the starch into a shorter linear glucan, thereby promoting the formation of RS by recrystallization. However, chain length of the starch debranched by pullulanase ranges from 6 to 60, resulting in the formation of a limited amount of short linear chains with double helix crystals and thereby a lower RS level. Based on this, in order to improve the level of RS in rice starch, the key is to obtain more short linear chains of moderate chain length to promote the molecular mobility, enabling easier arrangement and aggregation thereof to form a perfect resistant crystal.

SUMMARY

The following presents a simplified summary of the invention in order to provide a basic understanding of some aspects of the invention. This summary is not an extensive overview of the invention. It is not intended to identify critical elements or to delineate the scope of the invention. Its sole purpose is to present some concepts of the invention in a simplified form as a prelude to the more detailed description that is presented elsewhere.

The technical scheme adopted by the disclosure is as follows.

A green preparation method of rice resistant starch is characterized by: using rice starch as a substrate; and in turn using: β-amylase (BA, EC 3.2.1.2) from barley (*Hordeum vulgare*); glucoside transferase (TG, EC 2.4.1.24) from *Aspergillus niger*; and pullulanase (PUL, EC 3.2.1.41) from *Pullulanibacillus konaensis* below a gelatinization temperature to modify a chain structure of the rice starch, resulting in a number of short linear chains which are effectively arranged, aggregated, and recrystallized at 4° C. to form modified rice starch with high resistant starch content.

The state of rice starch granules plays a key role in the preparation of rice resistant starch. The gelatinization causes the starch granules to collapse completely, and the crystalline area almost disappears, which is not conducive to the formation of resistant starch. The invention modifies the rice starch at a temperature lower than the gelatinization temperature, which may not only reduce energy consumption, but also maintain the inherent crystal structure inside the starch granules.

The disclosure adopts a compound enzyme method (BA→TG→PUL) to modify rice starch at a temperature lower than the gelatinization temperature. First, BA hydrolyzes the α-(1→4) glycosidic bond in the rice starch from the non-reducing end of the chain Continuous removal of maltose units shortens the outer branch length of starch and produces β-glucan. Secondly, TG further catalyzes β-glucan through hydrolysis and transfer reactions to produce more β, T-glucans with short branched α-(1→6) glycosidic bonds. Finally, PUL cleaves the α-(1→6) glycosidic bond of β, T-glucan and produces a greater amount of short linear chains of appropriate length, which are suitable for forming perfect double-helix structures at 4° C. Resistant crystallites, which greatly increase the content of resistant starch and improve the digestibility of rice starch-based products.

In some embodiment, the disclosure provides a green preparation method of rice resistant starch. The method is characterized by using rice starch as a substrate; and in turn using: (a) β-amylase (BA, EC 3.2.1.2) from barley (*Hordeum vulgare*); (b) Glucoside transferase (TG, EC 2.4.1.24) from *Aspergillus niger*; and (c) pullulanase (PUL, EC 3.2.1.41) from *Pullulanibacillus konaensis* below a gelatinization temperature to modify a chain structure of the rice starch, resulting in a number of short linear chains which are effectively arranged, aggregated, and recrystallized at 4° C. to form modified rice starch with high resistant starch content.

In other embodiments, the disclosure provides a green preparation method of rice resistant starch. The method includes the following steps.

(1) Preparing the rice starch into a 10% (w/v) suspension and adjusting the suspension to pH 5.0.

(2) Adding β-amylase to the suspension, oscillating and hydrolyzing in water bath thermostatically, inactivating the enzyme, and adjusting the resulting enzymatic hydrolysate to pH 5.0.

(3) Adding glucosyltransferase to the enzymatic hydrolysate, oscillating and hydrolyzing in water bath thermostatically, inactivating the enzyme, and adjusting the resulting enzymatic hydrolysate to pH 5.0.

(4) Adding pullulanase to the enzymatic hydrolysate, oscillating and hydrolyzing in water bath thermostatically, inactivating the enzyme, and adjusting the resulting enzymatic hydrolysate to pH 7.0.

(5) Charging the enzymatic hydrolysate into absolute alcohol and keeping it still.

(6) Collecting precipitates by centrifugation and lyophilizing the resulting precipitates to obtain a product.

Optionally, in step (1), 20 g (dry weight) of rice starch is weighed, suspended in 200 mL of 0.02 mol/L sodium acetate buffer (pH 5.0, supplemented with 0.2 mL of 10% sodium azide), and stabilized in water bath for 0.5 hour at 50° C.

Optionally, in step (2), rice starch suspension is mixed with 1,300 U/g β-amylase, oscillated in water bath for 2 hours at 50° C., and subsequently mixed with 3 mL of 1 mol/L NaOH solution to inactivate the enzyme to terminate the reaction, followed by adjusting the resulting enzymatic hydrolysate to pH 5.0 with isometric HCl at the same concentration.

Optionally, step (3), the enzymatic hydrolysate obtained in step (2) is mixed with 1,650 U/g glucosyltransferase, oscillated in water bath for 4 to 12 hours at 50° C., and subsequently mixed with 3 mL of 1 mol/L NaOH solution to inactivate the enzyme to terminate the reaction, followed by adjusting the resulting enzymatic hydrolysate to pH 5.0 with isometric HCl at the same concentration.

Optionally, wherein in step (4), the enzymatic hydrolysate obtained in step (3) is mixed with 20 U/g pullulanase, oscillated in water bath for 12 hours at 55° C., and subsequently mixed with 3 mL of 1 mol/L NaOH solution to inactivate the enzyme to terminate the reaction, followed by adjusting the resulting enzymatic hydrolysate to pH 7.0 with isometric HCl at the same concentration.

Optionally, in step (5), under continuous stirring, the enzymatic hydrolysate obtained in step (4) is poured into three times the volume of absolute alcohol, and the resulting mixture stands still for 12 hours at 4° C.

Optionally, in step (6), precipitates are collected by centrifugation for 15 minutes at 5,000 rpm, subsequently washed with 90% ethanol three times, and finally lyophilized.

Optionally, the constant temperature water bath in step (2) is the same as the constant temperature water bath in step (3), and wherein the constant temperature water bath in step (3) is the same as the constant temperature water bath in step (4).

BRIEF DESCRIPTION OF THE DRAWINGS

Illustrative embodiments of the present disclosure are described in detail below with reference to the figures.

DETAILED DESCRIPTION

The following describes some non-limiting embodiments of the invention with reference to the accompanying drawings. The described embodiments are merely a part rather than all of the embodiments of the invention. All other embodiments obtained by a person of ordinary skill in the art based on the embodiments of the disclosure shall fall within the scope of the disclosure.

EXAMPLE 1

A Green Preparation Method of Rice Resistant Starch

It may include the following steps.

(1) Preparation of rice starch suspension. 20 g (dry weight) of rice starch is weighed accurately, suspended in 200 mL of 0.02 mol/L sodium acetate buffer (pH 5.0, supplemented with 0.2 mL of 10% sodium azide), and stabilized in water bath for 0.5 hour at 50° C.

(2) Enzymolysis with β-amylase. The rice starch suspension is mixed with 1,300 U/g β-amylase, oscillated in water bath for 2 hours at 50° C., and subsequently mixed with 3 mL of 1 mol/L NaOH solution to inactivate the enzyme to terminate the reaction, followed by adjusting the resulting enzymatic hydrolysate to pH 5.0 with isometric HCl at the same concentration.

(3) Enzymolysis with glucosyltransferase. The enzymatic hydrolysate obtained in the previous step is mixed with 1,650 U/g glucosyltransferase, oscillated in water bath for 4 to 12 hours at 50° C., and subsequently mixed with 3 mL of 1 mol/L NaOH solution to inactivate the enzyme to terminate the reaction, followed by adjusting the resulting enzymatic hydrolysate to pH 5.0 with isometric HCl at the same concentration.

(4) Pullulanase debranching. The enzymatic hydrolysate obtained in the previous step is mixed with 20 U/g pullulanase, oscillated in water bath for 12 hours at 55° C., and subsequently mixed with 3 mL of 1 mol/L NaOH solution to inactivate the enzyme to terminate the reaction, followed by adjusting the resulting enzymatic hydrolysate to pH 7.0 with isometric HCl at the same concentration.

(5) Recrystallization. Under continuous stirring, the final enzymatic hydrolysate is slowly poured into three times the volume of absolute alcohol, and the resulting mixture stands still for 12 hours at 4° C.

(6) Centrifugation, drying, and sieving: precipitates are collected by centrifugation for 15 minutes at 5,000 rpm, and subsequently washed with 90% ethanol three times. Finally, the precipitates are lyophilized, ground, and sieved through a 100-mesh sieve to obtain the rice resistant starch.

The enzymolysis with glucosyltransferase in step (3) lasted for 8 hours.

The modified starch obtained in the preferred scheme is used as a sample, and the modified starch is analyzed by modern analytical instruments such as high-performance anion exchange chromatography (HPAEC-PAD), X-ray diffractometer (XRD) and in vitro simulated digester with a pulsed amperometric detector. The relevant properties are measured and comparatively analyzed.

EXAMPLE 2

Using HPAEC-PAD to Analyze the Product Chain Length Distribution

Figure 1:
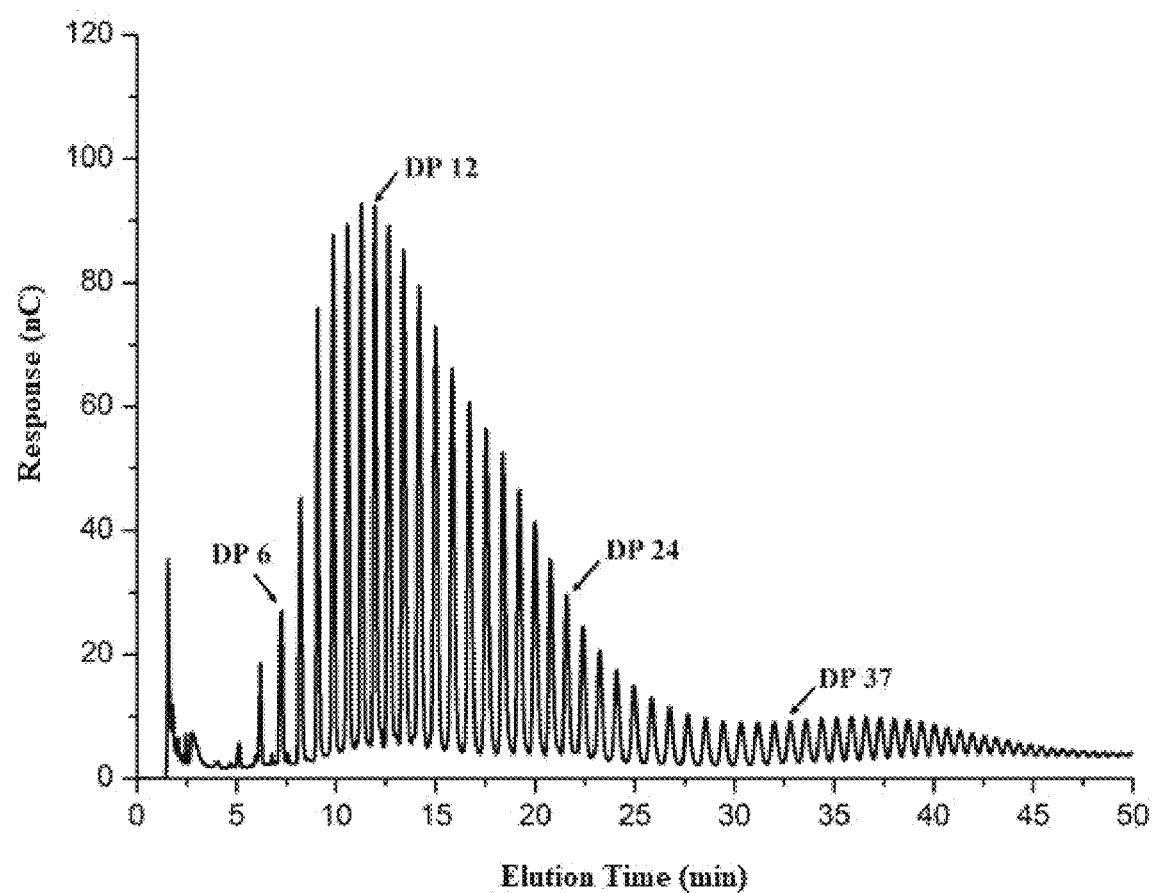
FIG. 1 is an HPAEC-PAD chromatogram of an original rice starch according to an embodiment of the disclosure.
Figure 2:
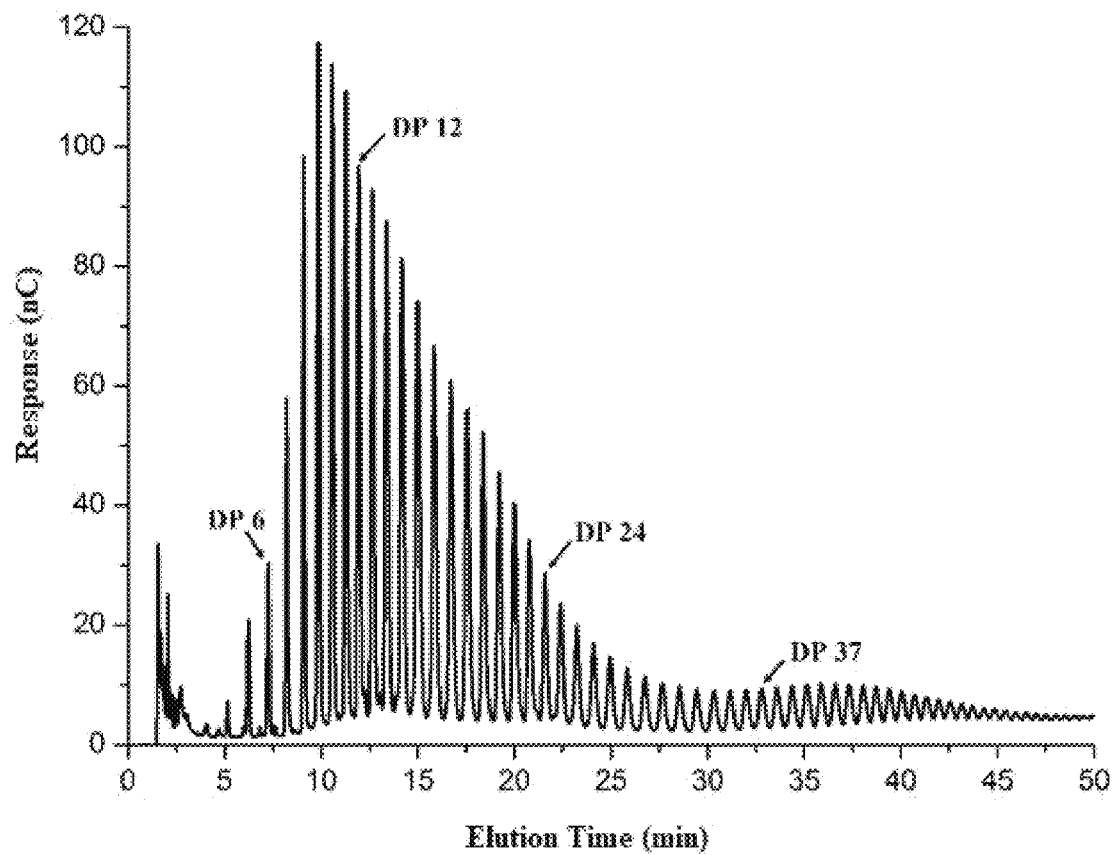
FIG. 2 is an HPAEC-PAD chromatogram of a modified starch according to an embodiment of the disclosure.

A pretreated sample (25 μL) is injected into an HPAEC-PAD system and eluted at a flow rate of 1 mL/min. Two kinds of eluents used are 150 mM NaOH (A) and 500 mM sodium acetate in 150 mM NaOH (B), respectively. Gradient elution is conducted by mixing eluent B with eluent A. The resulting chain length distribution diagrams are shown in FIGS. 1 and 2, and the results are summarized in the following Table 1.

TABLE 1

Chain length distribution of an original starch and a modified starch

| Sample | Chain length distribution ratio (%) | | | | | Average chain length |
|---|---|---|---|---|---|---|
| | DP < 6 | DP 6-12 | DP 13-24 | DP 25-36 | DP ≥ 37 | |
| Original Starch | 0.62 ± 0.02 | 24.50 ± 0.033 | 51.65 ± 0.02 | 13.37 ± 0.02 | 9.86 ± 0.03 | 21.37 ± 0.05 |
| Modified Starch | 1.34 ± 0.04 | 31.73 ± 0.02 | 48.87 ± 0.06 | 9.85 ± 0.10 | 8.21 ± 0.09 | 16.48 ± 0.07 |

It may be seen from Table 1 that the modified starch has more short chains and less relatively long chains, and the average chain length decreases significantly. The chain length of the modified starch peaks at between DP 9 and DP 11.

EXAMPLE 3

Using XRD to Analyze the Crystallinity of the Product

Figure 3:
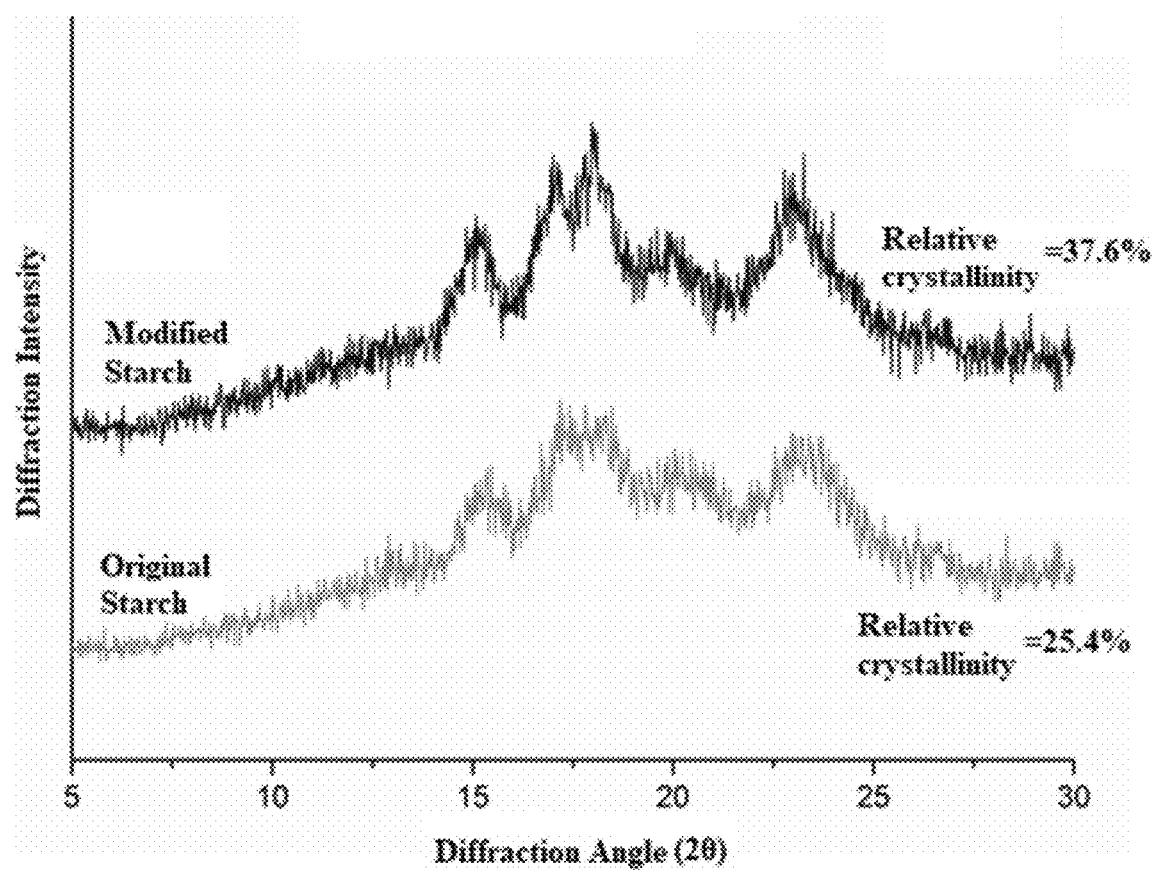
FIG. 3 is an X-ray diffraction diagram of an original rice starch and a modified starch according to an embodiment of the disclosure.

Crystalline properties of both native starch and modified starch are analyzed by a diffractometer. The diffractometer worked at 40 kV and 40 mA; diffraction angle (2θ) is 5° to 40°; scan rate is 10°/min. The ratio of crystallization peak area to total area of a diffraction pattern is the relative crystallinity of the sample. Results are shown in FIG. 3. As shown in FIG. 3, modification at a temperature below the gelatinization temperature will not destroy the inherent crystal structure of the starch, and both native starch and modified starch have properties of A-type crystals. Compared with the crystallinity of the native starch (25.4%), the crystallinity of the modified starch after enzymatic modification significantly increases to 37.6%. This indicates that short linear chains with DP 9-11 in modified starch granules are more likely to form double helix resistant crystals.

EXAMPLE 4

Analysis of Product Digestive Performance by In Vitro Digestion Equipment (NutraScan GI20, Next Instruments Pty Ltd., Australia)

In vitro digestibility and glycemic indexes (GIs) of both native starch and modified starch before and after cooking are determined by means of in vitro digestion equipment (NutraScan GI20, Next Instruments Pty Ltd., Australia). Each sample (equivalent to 50 mg of available carbohydrate) is weighed accurately in a 120 mL plastic sample container, and a heater block is set at 37° C.; rotational speed is 150 rpm. A program is set up as follows to determine in vitro digestion: charging 2 mL of α-amylase from porcine pancreatic juice (250 U/mL) and carbonate buffer (pH 7) into a sample cup, and incubating the mixture for 5 minutes at 37° C. to simulate oral digestion; (2) charging 5 mL of pepsin solution (1 mg/mL) from porcine gastric mucosa and 0.02 M hydrochloric acid (pH 2) into a sample cup, and incubating the mixture for 30 minutes at 37° C. to hydrolyze proteins; next, charging 5 mL of NaOH (0.02 M) into the sample cup to neutralize hydrolysates; (3) charging 25 mL of sodium acetate buffer (0.2 M, pH 6) and then 5 mL of enzyme solution (dissolving 130 mg of trypsin from porcine pancreas and 58.8 mg of amyloglucosidase from *Aspergillus niger* in 120 mL of 0.2 M sodium acetate solution (pH 6)) into each sample cup to simulate intestinal digestion. At different time intervals (20, 120, 180, 240, and 300 min), an aliquot of 1 mL of hydrolysates is injected into a glucose analyzer to determine a glucose concentration, and RDS, SDS, and RS are calculated for each starch sample. The GI of each sample is calculated as a percentage of available carbohydrate that could be transformed into glucose at 300 minutes of hydrolysis. Results are shown in Table 2. As shown in Table 2, compared with the native starch, the modified starch prepared by the process shows a significant increase in resistant starch content (84% before cooking versus 38% after cooking). In addition, the modified starch has a lower GI than the native starch. The above results indicate that compound enzyme modification process is an important step to reduce starch digestibility. The process improves starch chain mobility and increases opportunities of ordered orientation and rearrangement of short linear chains. This leads to a more perfect enzyme-resistant structure, greatly increasing the resistant starch content.

TABLE 2

Starch nutrition components and glycemic index (GI) of an original starch and a modified starch

| Sample | Starch Nutritional Component | | | | GI |
|---|---|---|---|---|---|
| | RDS/% | SDS/% | RS/% | (SDS + RS)/% | |
| Before Cooking | | | | | |
| Original Starch | 15.05 ± 0.30 | 15.47 ± 0.17 | 69.48 ± 0.47 | 84.95 ± 0.64 | 28.46 ± 0.75 |
| Modified Starch | 2.85 ± 0.19 | 12.83 ± 1.04 | 84.32 ± 1.24 | 97.15 ± 2.28 | 15.68 ± 1.24 |
| After Cooking | | | | | |
| Original Starch | 72.63 ± 0.55 | 17.53 ± 0.10 | 9.84 ± 0.65 | 27.37 ± 0.76 | 77.53 ± 0.36 |
| Modified Starch | 43.45 ± 0.79 | 18.27 ± 1.25 | 38.28 ± 2.04 | 56.55 ± 3.29 | 65.91 ± 0.99 |

Various embodiments of the disclosure may have one or more of the following effects.

In some embodiments, the disclosure may provide a green preparation method of rice resistant starch broadens the application field of rice starch and increases the added value of the original starch. Every year, there are more than 90 million tons of rice processing by-products that have not been reasonably developed and utilized in China, which has brought tremendous economic pressure and burden to our finances and grain depots. The invention may increase the economic value of starch and realize efficient industrialization of rice processing.

In other embodiments, the disclosure may provide a green preparation method of rice resistant starch, the raw material rice starch has some characteristics not possessed by other starches. Rice starch particles are small and uniform in size. The resistant starch made from rice starch has good color and light flavor. After gelatinization, the texture is very smooth and creamy. When added to food, it not only has many effects of dietary fiber, but also has a good taste. Compared with the rough taste of dietary fiber, this product is more easily accepted by consumers.

In further embodiments, the disclosure may provide a green preparation method of rice resistant starch, which is carried out at a temperature below the gelatinization temperature of rice starch, may reduce the energy consumption of starch gelatinization, and the yield (weight ratio of product to raw material) reaches more than 90%, In line with the requirements of enterprise economic benefits.

In some embodiments, the disclosure may provide a green preparation method of rice resistant starch, which uses a composite enzyme process to modify the starch chain. Compared with the single pullulanase debranching process, the disclosure adds β-amylase and glucoside transferase to modify the starch chain before the pullulanase debranching, thereby promoting the formation of a large number of short straight chains inside the starch granules It may fully recrystallize and other the content of resistant starch.

In other embodiments, the disclosure may provide a green preparation method of rice resistant starch, the content of the obtained resistant starch is relatively high. No additives are added to the entire process, and the product belongs to green and safe resistant starch. In addition, the equipment used is commonly used in starch processing, does not require any special equipment, the production cost is low, and is very suitable for industrial production.

In further embodiments, the content of resistant starch is high. The invention is simple in process, low in cost, low in energy consumption, high in yield, meets the requirements of economic benefits of the enterprise, has no additives, is green and safe, has good taste, and is easily accepted by consumers.

In some embodiments, the disclosure addresses the problem in prior art that the starch chain length after hydrolysis by a single enzyme (pullanase) is insufficient to form a high-content resistant starch, and provides a simple production process, strong operability, low production cost, safe and pollution-free Green preparation method of compound enzyme for rice resistant starch.

Many different arrangements of the various components depicted, as well as components not shown, are possible without departing from the spirit and scope of the present disclosure. Embodiments of the present disclosure have been described with the intent to be illustrative rather than restrictive. Alternative embodiments will become apparent to those skilled in the art that do not depart from its scope. A skilled artisan may develop alternative means of implementing the aforementioned improvements without departing from the scope of the present disclosure.

It will be understood that certain features and subcombinations are of utility and may be employed without reference to other features and subcombinations and are contemplated within the scope of the claims. Unless indicated otherwise, not all steps listed in the various figures need be carried out in the specific order described.

The disclosure claimed is:

1. A method of producing resistant starch, the method comprising:
   a) subjecting rice starch as the substrate to enzymatic digestion using β-amylase from barley, glucosidetransferase from *Aspergillus niger* and pullulanase from *Pullulanibacillus konaensis* to modify a chain structure of the rice starch, wherein the enzymatic digestion comprises the following steps in sequence:
      i) adding the β-amylase to the rice starch for reaction at a temperature lower than a gelatinization temperature of the rice starch to obtain a first mixture;
      ii) adding the glucosidetransferase to the first mixture obtained in step i) for reaction at a temperature lower than the gelatinization temperature of the rice starch to obtain a second mixture; and
      iii) adding the pullulanase to the second mixture obtained in step ii) for reaction at a temperature lower than the gelatinization temperature of the rice starch to obtain a third mixture; and
   b) recrystallizing the third mixture obtained in step iii) at 4° C. to form modified rice starch having an increased content of resistant starch.

2. The method of claim 1, wherein in step a) the rice starch is in the form of suspension.

3. The method of claim 2, wherein the suspension of the rice starch is at pH 5.0.

4. The method of claim 1, wherein thermostatic water bath is used from steps i) to iii) to keep reaction temperature constant for the enzymatic digestion.

5. The method of claim 1, wherein the first mixture in step i) is at pH 5.0; the second mixture in step ii) is at pH 5.0; and the third mixture in step iii) is at pH 7.0.

6. The method of claim 1, wherein a concentration of the β-amylase is 1300-1600 U/g; a concentration of the glucosidetransferase is 1600-1800 U/g; and a concentration of the pullulanase is 20-40 U/g.

* * * * *